United States Patent
Narizuka et al.

(10) Patent No.: US 6,362,372 B2
(45) Date of Patent: Mar. 26, 2002

(54) PROCESS FOR PRODUCING TRIFLUOROMETHYLBENZYLAMINES

(75) Inventors: Satoru Narizuka; Takashi Kume, both of Saitama (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 09/833,210

(22) Filed: Apr. 12, 2001

(30) Foreign Application Priority Data

Apr. 13, 2000 (JP) ......................................... 2000-112628

(51) Int. Cl.[7] ............................................. C07C 209/00
(52) U.S. Cl. ....................... 564/385; 564/389; 564/390; 564/391
(58) Field of Search ................................ 564/385, 389, 564/390, 391

(56) References Cited

U.S. PATENT DOCUMENTS 6,175,041 B1  1/2001  Takasaki et al.

OTHER PUBLICATIONS

Freifelder et al., "Preparation of Isomeric Trifluoromethyl-benzylamines", J. Pharm. Sci., 54 (1965), p. 1204.

*Primary Examiner*—Samuel Barts
(74) *Attorney, Agent, or Firm*—Crowell & Moring LLP

(57) ABSTRACT

The invention relates to a process for producing a trifluoromethylbenzylamine represented by the following general formula (1),

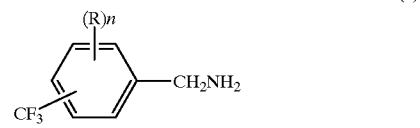
(1)

where each R independently represents a halogen selected from the group consisting of fluorine, chlorine, bromine and iodine, an alkyl group having a carbon atom number of 1–4, an alkoxy group having a carbon atom number of 1–4, an amino group, a hydroxyl group or a trifluoromethyl group, and n represents an integer from 0 to 4. The process includes hydrogenating a trifluoromethylbenzonitrile by hydrogen in an organic solvent in the presence of ammonia and a catalyst containing a platinum group element. This trifluoromethylbenzonitrile is represented by the following general formula (2),

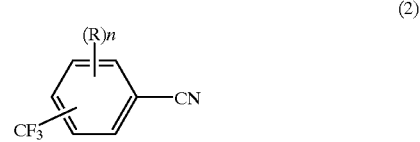
(2)

where R and n are defined as above. With this process, it is possible to obtain the trifluoromethylbenzylamine at an extremely high yield.

8 Claims, No Drawings

PROCESS FOR PRODUCING TRIFLUOROMETHYLBENZYLAMINES

BACKGROUND OF THE INVENTION

The present invention relates to a process for producing trifluoromethylbenzylamines useful in the pharmaceutical and agricultural chemical fields.

Numerous processes for obtaining primary amines by hydrogenation of nitrile compounds have been reported. In addition, numerous processes for obtaining primary amines of fluorine-containing aromatics from fluorine-containing aromatic nitrile compounds have also been reported.

J. Pharm. Sci., 54, 1204 (1965) discloses that a benzylamine (yield: 56–68.5%) is obtained by a catalytic hydrogenation of the corresponding trifluoromethylbenzonitrile in the presence of hydrogen chloride using a catalyst (palladium/carbon). In such a hydrogenation, selectivity is lowered, in case that a primary amine is obtained by a hydrogenation of a trifluoromethyl-containing nitrile compound. Therefore, a subsequent purification (e.g., distillation) becomes very complicated.

U.S. Pat. No. 6,175,041 B1 discloses a process for producing 3,5-bis(trifluoromethyl)benzylamine by a hydrogenation of 3,5-bis(trifluoromethyl)benzonitrile in the presence of ammonia in an organic solvent under a hydrogen pressurized condition (40 kg/cm$^2$) using a Raney catalyst. This process requires such a high pressure.

Processes for obtaining trifluoromethylbenzylamines from aromatic nitrile compounds having a trifluoromethyl group have problems that remain to be solved, and an industrially useful process for producing trifluoromethylbenzylamines has yet to be established.

SUMMARY OF THE INVENTION

It is therefore an object of the present invention to provide a process for producing a trifluoromethylbenzylamine easily and inexpensively.

According to the present invention, there is provided a process for producing a trifluoromethylbenzylamine represented by the following general formula (1),

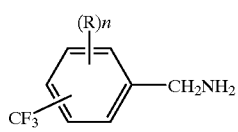

(1)

where each R independently represents a halogen selected from the group consisting of fluorine, chlorine, bromine and iodine, an alkyl group having a carbon atom number of 1–4, an alkoxy group having a carbon atom number of 1–4, an amino group, a hydroxyl group or a trifluoromethyl group, and n represents an integer from 0 to 4. The process comprises hydrogenating a trifluoromethylbenzonitrile by hydrogen in an organic solvent in the presence of ammonia and a catalyst comprising a platinum group element. The trifluoromethylbenzonitrile is represented by the following general formula (2),

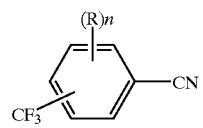

(2)

where R and n are defined as above. With this process, it is possible to obtain the trifluoromethylbenzylamine at an extremely high yield.

DESCRIPTION OF THE PREFERRED EMBODIMENTS

The trifluoromethylbenzonitrile represented by the general formula (2) used in the present invention is a benzonitrile having at least one trifluoromethyl group. This benzonitrile may also have a substituent group that is inactive under the conditions of the hydrogenation of the present invention. Examples of such substituent group include halogens (i.e., fluorine, chlorine, bromine and iodine), alkyl groups each having a carbon atom number of 1–4, alkoxy groups each having a carbon atom number of 1–4, amino groups, hydroxyl groups and trifluoromethyl groups. Specific examples of the trifluoromethylbenzonitrile include 2-trifluoromethylbenzouitrile, 3-trifluoromethylbenzonitrile, 4-trifluoromethylbenzonitrile, 2-bromo-5-trifluoromethylbenzonitrile, 2-chloro-5-trifluoromethylbenzonitrile, 2-fluoro-5-trifluoromethylbenzonitrile, 4-iodo-2-trifluoromethylbenzonitrile, 4-iodo-3-trifluoromethylbenzonitrile, 2-methoxy-5-trifluoromethylbenzonitrile, 3-methoxy-4-trifluoromethylbenzonitrile, 4-hydroxy-2-trifluoromethylbenzonitrile, 4-methoxy-3-trifluoromethylbenzonitrile, 2-amino-3-trifluoromethylbenzonitrile, 2-amino-5-trifluoromethylbenzonitrile, 2-amino-6-trifluoromethylbenzonitrile, 3-amino-5-trifluoromethylbenzonitrile, 4-amino-2-trifluoromethylbenzonitrile, 4-amino-3-trifluoromethylbenzonitrile, 2,3-bis(trifluoromethyl)benzonitrile, 2,4-bis(trifluoromethyl)benzonitrile, 2,5-bis(trifluoromethyl)benzonitrile, 2,6-bis(trifluoromethyl)benzonitrile, 3,4-bis(trifluoromethyl)benzonitrile, 3,5-bis(trifluoromethyl)benzonitrile, 2,3,6-tris(trifluoromethyl)benzonitrile, 2,4,6-tris(trifluoromethyl)benzonitrile, 2,3,4,6-tetraquis(trifluoromethyl)benzonitrile, 2-amino-4,6-bis(trifluoromethyl)benzonitrile, 4-amino-3,5-bis(trifluoromethyl)benzonitrile and 4-chloro-3 5-bis(trifluoromethyl)benzonitrile. Of these, 3,5-bis(trifluoromethyl)benzonitrile, 3-trifluoromethylbenzonitrile, and 4-trifluoromethylbenzonitrile are particularly preferable. These trifluoromethylbenzonitriles having trifluoromethyl groups can be produced by various processes. For example, 2-trifluoromethylbenzonitrile can be obtained by fluorinating 2-trichloromethylbenzonitrile with antimony trifluoride, while 4-trifluoromethylbenzonitrile can be obtained by heating 4-trifluoromethylaniline diazoate with K$_3$[Cu(CN)$_4$].

The reaction of the benzonitrile compound is conducted by catalytic hydrogenation. Although both heterogeneous and homogeneous catalysts can be used as the catalyst of the catalytic hydrogenation, heterogeneous catalysts are preferable in consideration of their ease of removal. The catalyst used in the process of the invention contains a metal (active species) that is a platinum group element selected from ruthenium, rhodium, palladium, osmium, iridium, and platinum. Thus, metals or metal oxides such as palladium or platinum oxide, or these supported on a carrier such as activated carbon, alumina or diatomaceous earth, can be used. Examples of the catalyst include palladium-loaded activated carbon, palladium hydroxide-loaded activated carbon, palladium-loaded barium sulfate, palladium-loaded calcium carbonate, palladium-loaded strontium carbonate, palladium black, palladium-loaded silica gel, platinum dioxide, platinum-loaded activated carbon, platinum black, ruthenium-loaded activated carbon and rhodium-loaded activated carbon. Although the amount of the catalyst may vary according to its type, it is preferably 0.0001–10 moles, more preferably 0.001–1 mole, per 100 moles of the benzonitrile compound represented by the general formula (2).

Examples of the reaction solvent include alcohols, hydrocarbons, ethers, carboxylic acids, esters, amides, and water. Typical examples of these solvents include methanol, ethanol, benzene, toluene, xylene, ethyl benzene, isopropyl benzene, tetralin, mesitylene, tetrahydrofuran, diethyl ether, acetic acid, ethyl acetate and dimethylformamide, and two or more types of these solvents can be used in combination.

The process of the present invention can be carried out under pressurization by hydrogen. Upon this, a pressure of 0.5–25 MPa is preferable, while that of 1–10 MPa is more preferable. If the reaction pressure is less than 0.5 MPa, a longer time is required for reaction. If the reaction pressure exceeds 25 MPa, although there are no problems in terms of the reaction, this is not preferable with respect to the strength of the apparatus, reaction procedure and pressurization procedure.

The process of the present invention can be carried out at −20 to 100° C., preferably −20 to 50° C., more preferably in the vicinity of room temperature. Here, room temperature refers to the temperature in the absence of heating or cooling. If the reaction temperature is below −20° C., the reaction requires a longer period of time. If the reaction temperature is above 100° C., the amount of reaction by-products increases and the yield of the target product decreases correspondingly, thus making this undesirable.

In the process of the present invention, the amount of ammonia added is preferably 1–30 parts by weight to 100 parts by weight of the trifluoromethylbenzonitrile as the starting material. Although liquid ammonia is normally used, it may also be introduced as a gas. In addition, basic substance(s) can also be added to the reaction system. Examples of basic substances that can be used include hydroxides, oxides, carbonates and so forth of alkaline metals or alkaline earth metals. Specific examples of such basic substances include sodium hydroxide, potassium hydroxide, lithium hydroxide, calcium hydroxide, magnesium hydroxide, barium hydroxide, sodium carbonate and potassium carbonate. Basic substance(s) can also be added to the reaction system in the form of an aqueous solution prepared to an arbitrary concentration.

The process of the present invention can be carried out either a batch operation or a continuous operation. In the case of using a batch operation, the reaction can be carried out, as follows. At first, predetermined amounts of the trifluoromethylbenzonitrile represented by the general formula (2), the catalyst containing a platinum group element, and an organic solvent are charged into a corrosion-resistant, pressure-proof reaction vessel made of stainless steel, glass or having a glass lining. Then, the atmosphere of the reaction vessel is replaced with an inert gas. Then, a predetermined amount of ammonia is added. After that, hydrogen is introduced by adding pressure to a predetermined pressure. Then, the reaction vessel is heated and held at a predetermined temperature with stirring, to carry out the reaction. As the reaction progresses, absorption of hydrogen occurs and the pressure inside the reaction vessel decreases. However, the pressure inside the reaction vessel can be maintained constant by continuously or intermittently introducing hydrogen. After confirming that absorption of hydrogen is no longer occurring, the reaction vessel is cooled, then the contents are removed, and then filtered to separate into an organic matter and the catalyst. The reaction product obtained in this manner is subjected to processing including rinsing with water, drying and distillation in accordance with routine methods, allowing the obtaining of the trifluorobenzylamine of high purity.

In general, polar solvents such as methanol have been used for the nitrile hydrogenation solvent. In that case, ammonia is frequently added for the purpose of inhibiting secondary amines formed as a by-product in nitrile hydrogenations. Since the solubility of ammonia is high in these polar solvents, they are also used for reasons of easier workability during charging. However, in the case of the trifluoromethylbenzonitriles of the present invention, polar solvents such as alcohol cause an addition reaction to the trifluoromethylbenzonitriles, and since, for example, methoxyimine is generated in the case of methanol, the use of such polar solvents may result in a significant decrease in yield. Moreover, the reaction products (e.g., methoxyimine) of this addition reaction may turn into dimers and trimers, due to, heating and so forth during distillation in following isolation procedures. However, at the reaction temperature suitable for conducting the process of the invention, there is no occurrence of addition of solvent to the starting material, thereby making it possible to obtain the target product (i.e., the trifluoromethylbenzylamine) at high yield.

The following nonlimitative examples are illustrative of the present invention.

EXAMPLE 1

At first, a 1-liter autoclave equipped with a mechanical stirrer was charged with 50 g (0.21 mol) of 3,5-bis (trifluoromethyl)benzonitrile, 200 ml of 2M-ammoniacal methanol solution (containing 400 mmol of ammonia), and 3 g of a catalyst (i.e., a carbon powder (50% wet) carrying thereon 5% palladium), followed by introduction of hydrogen to have a pressure of 1 MPa. Then, the reaction mixture was stirred, while the reaction temperature was maintained at 20° C. and while hydrogen was gradually introduced into the autoclave in a manner to maintain the total pressure at 1 MPa. After conducting the reaction for 5.3 hr, the reaction was stopped, followed by removing the catalyst by filtration. As a result of analyzing the obtained reaction liquid by gas chromatography, 3,5-bis(trifluoromethyl)benzylamine was formed at a yield of 87.0%.

EXAMPLE 2

At first, a 1-liter autoclave equipped with a mechanical stirrer was charged with 200 g (0.84 mol) of 3,5-bis (trifluoromethyl)benzonitrile, 200 ml of methanol, and 6 g of a catalyst (i.e., a carbon powder (50% wet) carrying thereon 5% palladium), followed by introduction of 14 g of liquid ammonia and then introduction of hydrogen to have a pressure of 1 MPa. Then, the reaction mixture was stirred, while the reaction temperature was maintained at 20° C. and while hydrogen was gradually introduced into the autoclave in a manner to maintain the total pressure at 1 MPa. After conducting the reaction for 3 hr, the reaction was stopped, followed by removing the catalyst by filtration. As a result of analyzing the obtained reaction liquid by gas chromatography, 3,5-bis(trifluoromethyl)benzylamine was formed at a yield of 85.1%.

The entire disclosure of Japanese Patent Application No. 2000-112628 filed on Apr. 13, 2000, including specification, claims and summary, is incorporated herein by reference in its entirety.

What is claimed is:

1. A process for producing a trifluoromethylbenzylamine represented by the following general formula (1), said process comprising hydrogenating a trifluoromethylbenzonitrile represented by the following general formula (2) by hydrogen in an organic solvent in the presence of ammonia and a catalyst comprising a platinum group element,

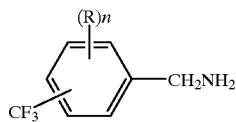
(1)

where each R independently represents a halogen selected from the group consisting of fluorine, chlorine, bromine and iodine, an alkyl group having a carbon atom number of 1–4, an alkoxy group having a carbon atom number of 1–4, an amino group, a hydroxyl group or a trifluoromethyl group, and n represents an integer from 0 to 4,

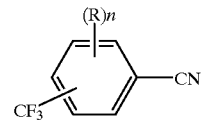
(2)

where R and n are defined as above.

2. A process according to claim 1, wherein said trifluoromethylbenzonitrile is selected from the group consisting of 3,5-bis(trifluoromethyl)benzonitrile, 3-trifluoromethylbenzonitrile, and 4-trifluoromethylbenzonitrile.

3. A process according to claim 1, wherein said platinum group element is selected from the group consisting of ruthenium, rhodium, palladium, osmium, iridium, and platinum.

4. A process according to claim 1, wherein said catalyst further comprises a carrier carrying thereon said platinum group element.

5. A process according to claim 1, wherein said catalyst comprises an activated carbon carrying thereon palladium.

6. A process according to claim 1, wherein said catalyst is in an amount of 0.0001 to 10 moles per 100 moles of said trifluoromethylbenzonitrile.

7. A process according to claim 1, wherein said hydrogenating is conducted under a pressurized condition caused by an addition of said hydrogen.

8. A process according to claim 1, wherein said ammonia is in an amount of from 1 to 30 parts by weight per 100 parts by weight of said trifluoromethylbenzonitrile.

* * * * *